United States Patent
Shah et al.

(10) Patent No.: US 9,220,686 B2
(45) Date of Patent: Dec. 29, 2015

(54) MULTIPARTICULATE L-MENTHOL FORMULATIONS AND RELATED METHODS

(71) Applicant: Zx Pharma, LLC, Boca Raton, FL (US)

(72) Inventors: Syed M. Shah, Boca Raton, FL (US); Fred Hassan, Boca Raton, FL (US); Daniel Hassan, Boca Raton, FL (US); Sarah Hassan, Boca Raton, FL (US)

(73) Assignee: Zx Pharma, LLC, Boca Raton, FL (US)

( * ) Notice: Subject to any disclaimer, the term of this patent is extended or adjusted under 35 U.S.C. 154(b) by 0 days.

(21) Appl. No.: 14/535,598

(22) Filed: Nov. 7, 2014

(65) Prior Publication Data

US 2015/0064261 A1    Mar. 5, 2015

Related U.S. Application Data

(63) Continuation of application No. 14/033,737, filed on Sep. 23, 2013, now Pat. No. 8,911,780, which is a continuation of application No. 13/367,747, filed on Feb. 7, 2012, now Pat. No. 8,568,776.

(60) Provisional application No. 61/441,716, filed on Feb. 11, 2011, provisional application No. 61/486,523, filed on May 16, 2011, provisional application No. 61/880,294, filed on Sep. 20, 2013, provisional application No. 61/815,073, filed on Apr. 23, 2013.

(51) Int. Cl.

| | |
|---|---|
| A61K 9/26 | (2006.01) |
| A61K 9/14 | (2006.01) |
| A61K 31/045 | (2006.01) |
| A61K 31/353 | (2006.01) |
| A61K 31/57 | (2006.01) |
| A61K 9/50 | (2006.01) |
| A61K 45/06 | (2006.01) |
| A61K 31/05 | (2006.01) |
| A61K 31/573 | (2006.01) |
| A61K 31/606 | (2006.01) |
| A61K 36/23 | (2006.01) |
| A61K 31/352 | (2006.01) |
| A61K 36/534 | (2006.01) |

(52) U.S. Cl.
CPC . *A61K 9/14* (2013.01); *A61K 9/145* (2013.01); *A61K 9/5026* (2013.01); *A61K 9/5073* (2013.01); *A61K 31/045* (2013.01); *A61K 31/05* (2013.01); *A61K 31/352* (2013.01); *A61K 31/353* (2013.01); *A61K 31/57* (2013.01); *A61K 31/573* (2013.01); *A61K 31/606* (2013.01); *A61K 36/23* (2013.01); *A61K 45/06* (2013.01); *A61K 36/534* (2013.01)

(58) Field of Classification Search
USPC .......................... 424/468, 469, 474; 568/829
See application file for complete search history.

(56) References Cited

U.S. PATENT DOCUMENTS

| | | |
|---|---|---|
| 4,687,667 A | 8/1987 | Rhodes et al. |
| 4,786,505 A | 11/1988 | Lovgren et al. |
| 5,362,745 A | 11/1994 | Graziella |
| 5,397,573 A | 3/1995 | Kajs et al. |
| 5,418,010 A | 5/1995 | Janda et al. |
| 5,498,423 A | 3/1996 | Zisapel |
| 5,840,332 A | 11/1998 | Lerner et al. |
| 6,139,877 A | 10/2000 | Debregeas et al. |
| 6,306,435 B1 | 10/2001 | Chen et al. |
| 6,365,185 B1 | 4/2002 | Ritschel et al. |
| 6,423,349 B1 | 7/2002 | Sherratt et al. |
| 6,531,152 B1 | 3/2003 | Lerner et al. |
| 6,632,451 B2 | 10/2003 | Penhasi et al. |
| 6,726,927 B2 | 4/2004 | Chen |
| 6,972,132 B1 | 12/2005 | Kudo et al. |
| 7,041,316 B2 | 5/2006 | Chen |
| 7,048,945 B2 | 5/2006 | Percel et al. |
| 7,115,282 B2 | 10/2006 | Shefer et al. |
| 7,670,619 B2 | 3/2010 | Mihaylov |
| 7,670,624 B2 | 3/2010 | Tsutsumi et al. |
| 7,790,215 B2 | 9/2010 | Sackler et al. |
| 7,790,755 B2 | 9/2010 | Akiyama et al. |
| 7,803,817 B2 | 9/2010 | Kostadinov et al. |
| 7,829,122 B2 | 11/2010 | Bruna et al. |
| 7,838,027 B2 | 11/2010 | Rao et al. |
| 8,337,811 B1 | 12/2012 | Sung et al. |
| 8,361,439 B1 | 1/2013 | Sung et al. |
| 8,524,257 B2 | 9/2013 | Nowak et al. |

(Continued)

FOREIGN PATENT DOCUMENTS

| | | |
|---|---|---|
| CN | 1886119 B | 4/2015 |
| EP | 0015334 B1 | 5/1982 |

(Continued)

OTHER PUBLICATIONS

Yuasa et al., Whisker Growth of I-menthol in coexistence with various excipents, International Journal of Pharmacutics 203, (2000), pp. 203-210, Tokyo, Japan.

(Continued)

*Primary Examiner* — Ali Soroush
(74) *Attorney, Agent, or Firm* — Christopher M. Ramsey; GrayRobinson, P.A.

(57) ABSTRACT

A multiparticulate dosage form includes a plurality of individual spheroidal enteric coated particulates having (a) a diameter of 0.1 to 2.5 mm; (b) a solid core containing an effective amount of a combination of an L-menthol source and a terpene-based essential oil; (c) a continuous proteinaceous subcoating over the core; and (d) an enteric coating over the subcoating. The multiparticulate dosage form can be used to treat gastrointestinal disorders.

21 Claims, 2 Drawing Sheets

(56) References Cited

U.S. PATENT DOCUMENTS

| | | | |
|---|---|---|---|
| 8,535,640 | B1 | 9/2013 | Sung et al. |
| 8,545,880 | B2 | 10/2013 | Li et al. |
| 8,568,776 | B2 | 10/2013 | Shah et al. |
| 8,574,544 | B1 | 11/2013 | Sung et al. |
| 8,808,736 | B2 | 8/2014 | Shah et al. |
| 2001/0038863 | A1 | 11/2001 | Jaenicke |
| 2002/0114832 | A1 | 8/2002 | Herrmann et al. |
| 2002/0192285 | A1 | 12/2002 | Mulye |
| 2003/0040539 | A1 | 2/2003 | Zisapel |
| 2003/0143272 | A1 | 7/2003 | Waterman |
| 2003/0207851 | A1 | 11/2003 | Wei |
| 2004/0052846 | A1 | 3/2004 | Prater et al. |
| 2004/0062778 | A1 | 4/2004 | Shefer et al. |
| 2005/0069579 | A1 | 3/2005 | Kamaguchi et al. |
| 2005/0129761 | A1 | 6/2005 | Venkata Ramana Rao et al. |
| 2005/0164987 | A1 | 7/2005 | Barberich |
| 2005/0181047 | A1 | 8/2005 | Romero |
| 2005/0202079 | A1 | 9/2005 | Bielski et al. |
| 2005/0281876 | A1 | 12/2005 | Li et al. |
| 2006/0009465 | A1 | 1/2006 | Edgar et al. |
| 2006/0127489 | A1 | 6/2006 | Crothers et al. |
| 2006/0210631 | A1 | 9/2006 | Patel et al. |
| 2006/0246134 | A1 | 11/2006 | Venkatesh |
| 2006/0257469 | A1 | 11/2006 | Bulka |
| 2006/0280795 | A1 | 12/2006 | Penhasi et al. |
| 2007/0231388 | A1 | 10/2007 | Anstett-Klein et al. |
| 2007/0292510 | A1 | 12/2007 | Huang |
| 2008/0139510 | A1 | 6/2008 | Rose |
| 2008/0152719 | A1 | 6/2008 | Petereit et al. |
| 2008/0166416 | A1 | 7/2008 | Lizio et al. |
| 2008/0199518 | A1 | 8/2008 | Ku et al. |
| 2008/0299199 | A1 | 12/2008 | Bar-Shalom |
| 2009/0004262 | A1 | 1/2009 | Shaw et al. |
| 2009/0004281 | A1 | 1/2009 | Nghiem et al. |
| 2009/0137670 | A1 | 5/2009 | Kramer et al. |
| 2009/0227670 | A1 | 9/2009 | Berg |
| 2009/0238905 | A1 | 9/2009 | Gurney et al. |
| 2009/0246301 | A1 | 10/2009 | Ehrenpreis et al. |
| 2010/0119601 | A1 | 5/2010 | McCarty |
| 2010/0183713 | A1 | 7/2010 | Tsutsumi et al. |
| 2010/0203134 | A1 | 8/2010 | Chenevier et al. |
| 2010/0298379 | A1 | 11/2010 | Jacobsen |
| 2011/0053866 | A1 | 3/2011 | Duffield et al. |
| 2011/0064830 | A1 | 3/2011 | Muller et al. |
| 2011/0081451 | A1 | 4/2011 | Siegel et al. |
| 2012/0207842 | A1 | 8/2012 | Shah et al. |
| 2012/0277323 | A1 | 11/2012 | Kumar et al. |
| 2012/0301541 | A1 | 11/2012 | Haronsky et al. |
| 2012/0301546 | A1 | 11/2012 | Hassan |
| 2013/0230597 | A1 | 9/2013 | Cook et al. |
| 2014/0178468 | A1 | 6/2014 | Shear et al. |

FOREIGN PATENT DOCUMENTS

| | | |
|---|---|---|
| EP | 1953625 A | 8/2008 |
| EP | 1958625 A1 | 8/2008 |
| WO | 9959544 | 11/1999 |
| WO | 2005027878 A | 3/2005 |
| WO | 2005032513 A2 | 4/2005 |
| WO | 2007012856 A | 2/2007 |
| WO | 2008057802 A | 5/2008 |
| WO | 2008134807 A | 11/2008 |
| WO | 2009077749 A | 6/2009 |
| WO | 2010144943 A | 12/2010 |
| WO | 2012109216 A | 8/2012 |
| WO | 2012170488 A | 12/2012 |
| WO | 2012170611 A | 12/2012 |

OTHER PUBLICATIONS

ISR for PCT/US12/41226, Issued Aug. 16, 2012.
Kim et al. (The Influence of Surelease and Sodium Alginate on the In-Vitro Release of Tamsulosin Hydrochloride in Pellet Dosage Form., J Pharm Pharmacol, Jun. 2005; 57(6): 735-42.
Office Action for U.S. Appl. No. 14/524,326, Issued Apr. 23, 2015.
Abdul et al., A Flexible Technology of Modified-Rlease Drugs: Multiple-Unite Pellet System (MUPS), J Controlled Release 147: 2-16 (2010).
Baranuskiene et al., Flavor Retention of Peppermint (*Mentha piperita* I.) Essential Oil Spray-Dried ni Modified Starches during Encapsulation and Storage, J. Agric. Food Chem., 2007, 55, 3027-3036.
Benes et al., Transmucosal, Oral Controlled-Release and Transdermal Drug Administration in Human Subjects: A Corssover Study with Melatonin, Journal of Pharmaceutical Sciences/1115, vol. 86, No. 10, Oct. 1997.
Bogentoft et al., Influence of Food on the Absorption of Acetylsalicylic Acid From Enteric-Coated Dosage Forms, European J. Clin. Pharmacol., 14, 351-355, 1978.
Cellulose acetate phthalate enter coating (enerexusa.com/articles/enteric_coating.htm., last visit Feb. 6, 2014).
Chourasia et al., Pharmaceutical Approaches to Colon Targeted Drug Delivery Systems, J Pharm Pharmaceut Sci 6: 33-66 (2003).
Clark et al., Variations in Composition of Peppermint Oil in Relation to Production Areas, Economic Botany 35(1), 1981, pp. 59-69, Bronx, NY, USA.
Committee for Proprietary Medicinal Products, Note for Guidance on Quality of Modified Release Products: A: Oral Dosage Forms, B: Transdermal Dosage Forms, Jul. 29, 1999, The European Agency for the Evaluation of Medicinal Products, London.
Dey et al., Multiparticulate Drug Deliver Systems for Controlled Release, Tropical Journal of Pharmaceutical Research, Sep. 2008; 7(3): 1067-1075, Pharmacotherapy Group, Faculty of Pharmacy, University of Benin, Benin City, 300001 Nigeria.
Digenis, Geroge A., The in vivo behavior of multiparticulate versus single unit dose formulations, presented at Capsugel's Symposium in Seoul (Apr. 10, 1990) and Tokyo (Apr. 12, 1990).
Dong et al., Effect of processing parameters on the formation of spherical multinuclear microcapsules encapsulating peppermint oil by coacervation, Journal of Microencapsulation, Nov. 2007; 24(7): 634-646.
Faroongsarng et al., The Swelling & Water Uptake of Tablets III: Moisture Sorption Behavior of Tablet Disintegrants, Drug Development and Industrial Pharmacy, 20(5), 779-798, (1994).
Final Report on the Safety Assessment of *Mentha piperita* (Peppermint) Oil, *Mentha piperita* (Peppermint) Leaf Extract, *Mentha piperita* (Peppermint) Leaf, and *Mentha piperita* (Peppermint) Leaf Water, International Journal of Toxicology, 2001 20:61, online version at http://ijt.sagepub.com/content/20/3/_suppl/61.
Galeotti et al., Menthol: a natural analgesic compound, Neuroscience Letters 322 (2002), pp. 145-148, Florence, Italy.
Grigoleit et al., Gastrointestinal clinical pharmacology of peppermint oil, Phytomedicine 12, (2005), pp. 607-611, Wiesbaden, Germany.
International Search Report of Feb. 16, 2014 for PCT/US2013/061141.
International Search Report of Feb. 4, 2014 for PCT/US2013/061146.
International Search Report of Feb. 6, 2014 for PCT/US2013/061141.
International Search Report of Jan. 29, 2014 for PCT/US2013/000217.
Juergens, et al., The Anti-Inflammatory Activity of L-Menthol Compared to Mint Oil in Human Monocytes In Vitro: A Novel Perspective for Its Therapeutic Use in Inflammatory Diseases, Eur J. Med Res (1998) 3: 539-545, Dec. 16, 1998.
Kellow et al., Altered Small Bowel Motility in Irritable Bowel Syndrome is Corrected With Symptoms, Gastroenterology, 1987, vol. 92, pp. 1885-1893, Rochester, Minnesota, USA.
Kline et al., Enteric-Coated pH-dependent peppermint oil capsules for the treatment of irritable bowel syndrome in children, J Pediatr 2001; 138: 125-8.
Lee et al, Design and evaluationof an oral controlled release delivery systme for melatonin in humans subjects, International Journal of Pharmaceutics 124 (1995) 119-127, College of Pharmacy, Kangwon National University, Chuncheon, South Korea, Department of Pharmaceutics, College of pHarmacy, Oregeon State University,

(56) References Cited

OTHER PUBLICATIONS

Corvallis OR 97331-3507, USA, Department of Psychiatry, School of Medicine, Oregon Health Sciences University, Portland, OR, USA.

Lee et al., Formulation and Release Characteristics of Hydroxpropyl Methycellulose Matrix Tablet Containing Melatonin, Drug Development and Industrial Pharmacy, 25(4), 493-501 (1999), Biological Rhythm and Controlled Release Laboratory, College of Pharmacy, Kangwon National University, Chuncheon 200-709, Korea.

Liu et al., pH-resonsive amphiphilic hydrogel networks with IPN structure; A strategy for controlled drug release, International Journal of Pharmaceutics 308 (2006) 205-209, Department of Applied Chemistry, School of Science, Northwestern Polytechnic University, Xi'an 710072, PR China.

MacPherson et al., More than cool: promiscuous relationships of menthol and other sensory compounds, Mol. Cell. Neurosci, vol. 32, 2006, pp. 335-343.

McIntyre et al., Melatonin Rhythm in Human Plasma and Saliva, Journal of Pineal Research 4:177-183 (1987), Psychoendocrine Research Unit, Department of Psychiatry, Austin Hospital Heidelbert (I.M.M., T.R.N., G.D.B.), and Department of Psychology, Brain Behaviour Research Institute, Latrobe University, Bundoora (S.M. A.), Victoria, Australia.

Menthols (inchem.org/documents/sids/sids/MENTHOLS.pdf, lat visit Feb. 6, 2014).

Micklefield, et al., Effects of Peppermint Oil and Caraway Oil on Gastroduodenal Motility, Phytother. Res. 14, 20-23 (2000).

Office Action for U.S. Appl. No. 14/033,713 issued May 14, 2014.
Office Action for U.S. Appl. No. 14/033,737 issued Apr. 23, 2014.
Office Action for U.S. Appl. No. 14/064,685 issued Sep. 24, 2014.
Office Action for U.S. Appl. No. 14/064,685 issued Mar. 7, 2014.

Pilbrant et al., Development of an oral formulation of omeprazole, Scand J. Gastroenterol, 1985, vol. 20 (suppl. 108, pp. 113-120, Molndal, Sweden.

Pittler et al., Peppermint Oil for Irritable Syndrome: A Critical Review and Metaanalysis, The American Journal of Gastroenterology, vol. 93, No. 7, 1998, 1131-1135.

Rees et al., Treating irritable bowel syndrome with peppermint oil, British Medical Journal, Oct. 6, 1979.

Rohloff et al., Effect of Harvest Time and Drying Method of Biomass Production, Essential Oil Yield, and Quality of Peppermint (*Mentha* x *piperita* L.), J. Agric. Food Chem., 2005, vol. 53, pp. 4143-4148 Hedmark, Norway.

RXMED: Pharmaceutical Information—Colpermin, Peppermint Oil Symptomatic Relief of Irritable Bowel Syndrome, Jan. 4, 2010.

Sibanda et al., Experimental Design for the Formulation and Optimization of Novel Cross-Linked Oilispheres Developed for In Vitro Site-Specific Release of Mentha piperita Oil, AAPS PharmSciTech 2004; 5(1) Article 18 (http://www.aapsharmscitech.org, submitted Nov. 5, 2003, Accepted Feb. 18, 2004.

Somerville et al., Delayed release peppermint oil capsules (Colpermin) for the spastic colon syndrome: a pharmacokinetic study, Br. J. clin. Pharmac., (1984), vol. 18, pp. 638-640, Ipswich, United Kingdom.

Stevens et al., The short term natural history of irritable bowel syndrome: a time series analysis, Behav. Res. Ther., vol. 35, No. 4, pp. 319-326, 1997, Albany, NY, USA.

Thomposon, Shaun, List of Proton Pump Inhibitors, Mar. 12, 2011, http://www.livestrong.com/article/26705-list-proton-pump-inhibitors.

Tran et al., New findings on melatonin absorption and alterations by pharmaceutical excipients using the Ussing chamber technique with mounted rat gastrointestinal segments, International Journal of Pharmaceuticals 378 (2009) pp. 9-16, Bioavailability Control Laboratory, College Pharmacy, Kangwon National University, Chuncheon 200-701, Republic of Korea.

Trimble et al., Heightened Visceral Sensation in Functional Gastrointestinal Disease Is Not Site-Specific, Digestive Diseases and Sciences, vol. 40, No. 8, Aug. 1995, pp. 1607-1613.

White et al., A pharmacokinetic comparison of two delayed-release peppermint oil preparations, Colpermin and Mintec, for treatment of the irritable bowel syndrome, International Journal of Pharmaceutics, vol. 40, 1987, pp. 151-155, Ipswich, United Kingdom.

MULTIPARTICULATE L-MENTHOL FORMULATIONS AND RELATED METHODS

CROSS-REFERENCE TO RELATED APPLICATIONS

This is a continuation of U.S. application Ser. No. 14/033,737, filed Sep. 23, 2013, which claims priority to U.S. provisional application 61/815,073, filed Apr. 23, 2013 and U.S. provisional application 61/880,294, filed Sep. 20, 2013, and which is a continuation-in-part of U.S. application Ser. No. 13/367,747, filed Feb. 7, 2012, which claims priority to U.S. provisional Application No. 61/441,716, filed Feb. 11, 2011, and U.S. provisional Application No. 61/486,523, filed May 16, 2011. Each of these prior applications is incorporated by reference herein in its entirety.

FIELD OF THE INVENTION

The invention relates to multiparticulate formulations for delivering L-menthol to the intestines, and, more particularly, to enteric coated L-menthol multiparticulate formulations and related methods.

BACKGROUND

Essential oils have been used for their bioactivity for quite some time. Some essential oils are currently being used as medicaments. For example the plants *mentha piperita* or *mentha arvensis*, are the two primary sources of peppermint oil. Peppermint oil is effective at treating the symptoms of gastrointestinal disorders such as irritable bowel syndrome (IBS), functional dyspepsia (FD), gastro paresis (GP), Crohn's disease (CD) and ulcerative colitis (UC). These symptoms can include pain, discomfort, bloating, constipation, and/or diarrhea. Clinical trials have demonstrated significant alleviation of the symptoms associated with IBS through the use of peppermint oil in single-unit capsules coated with the cellulose acetate-phthalate enteric polymer or other enteric-coating polymers.

For maximal efficacy in the treatment of IBS, FD, GP, CD and UC, and to avoid related complications, peppermint oil should be locally delivered to various sections of the intestines (i.e. duodenum, small intestine, ileum or large intestine [i.e. colon]), while avoiding the stomach. If peppermint oil is released from its dosage form prior to passing through the pyloric sphincter into the intestines, it can irritate the mucous membranes in the upper digestive tract. Releasing peppermint oil directly into the stomach can cause heartburn (gastric irritation) and gastro-esophogeal reflux disease. Therefore, since peppermint oil is usually administered orally, it should preferably be prepared with an enteric coating.

Enteric-coated single-unit capsules for treating irritable bowel syndrome and functional dyspepsia that contain peppermint oil currently exist. But, even though the enteric coated single-unit capsules are meant to delay the release of peppermint oil until after the capsule enters the intestines, this approach to treating gastrointestinal (GI) disorders has several drawbacks. The drawbacks include premature release of the peppermint oil from the capsule in the stomach, resulting in heartburn. Also, accidental chewing of the capsule causes the enteric coat to rupture prematurely and release the oil in the stomach.

The oil that is released from single-unit capsules is typically dissolved in cooking oil (such as peanut oil) to modify its release in the intestines. The peppermint oil (dissolved in cooking oil) released from single unit capsules, does not dissolve in the aqueous contents of the stomach but forms a layer of oil which floats on top of the aqueous phase in the stomach. This increase the likelihood of the peppermint oil plus cooking oil regurgitating into the esophageal area and causing reflux.

Using current formulations of peppermint oil, significant doses are required to achieve an efficacious concentration of peppermint oil in the body. For example, each of the above referenced capsules contains about 200 mg of peppermint oil and must be taken three times a day, 30-60 minutes prior to a meal. The dose can be increased to two capsules taken three times daily in some situations.

Enteric-coated peppermint oil is typically administered as a single-unit capsule formulation. However, in a single-unit formulation, the amount of peppermint oil absorbed by the intestines can vary from dose to dose for several reasons. First, single-unit enteric capsule formulation can get attached to the esophagus because of the muco-adhesive properties of the enteric coat and, therefore, not enter the stomach within the desired time frame. The single-unit enteric coated capsules, like enteric coated single-unit tablets, have been shown to not release the active ingredient from the single-unit formulation because the single-unit's size is too large to pass through the constriction in the stomach's pylorus valve, until the inter-digestive or house cleaning phase. The enteric coat of the capsule may also prematurely crack or rupture because of the force created by the swelling of the gelatin or hypromellose used to form the capsule shell due to its water of hydration, against the outer enteric coat. Because peppermint oil containing capsules have a lower specific gravity than the stomach contents, they tend to float rather than settle and pass through the pylorus constriction between the stomach and the lower intestines, unreliably and only during the inter-digestive phase.

Non-disintegrating tablets or capsules given with food may stay in the stomach for long times, up to 10 to 15 hours, before they are emptied into the small intestine. Small particles, with diameters less than or about 3 mm, are emptied from the stomach more regularly, regardless of whether they are given with food. The 10 to 15 hours that an enteric coated hard gelatin or hypromellose capsule may get exposure to gastric conditions in a fed state may cause the enteric coat to rupture and the hard gelatin (or hypromellose) seal coat to dissolve, resulting in the peppermint oil being released in the stomach and causing heartburn or gastric irritation.

Even if the single-unit enteric coated capsule passes through the pylorus intact in a timely fashion, when it reaches the small intestine, the coating dissolves and a bolus of oil is released. This dosage dumping is a situation in which the active ingredient is released and gives very high local exposure in a segment of the intestine, is also undesirable because it prevents uniform and steady exposure of peppermint oil in the GI lumen. This high local exposure to one section of the GI lumen may actually aggravate symptoms of IBS.

Single-unit formulations are also significantly influenced by the presence of food in the stomach. Gastric emptying rates of single-unit doses are erratic and unpredictable. Single-unit enteric-coated tablets or capsules taken with food may stay in the stomach for many hours before being emptied into the small intestine. As a result, single-unit formulations present both high inter and intra-subject variability with respect to the pharmacokinetics (PK) and local bioavailable concentration of active ingredient. According to regulatory guidelines, enteric-coated single-unit capsules can never be bioequivalent with multiple-unit enteric-coated dosage forms. A single-unit enteric preparation containing peppermint oil was disclosed in U.S. Pat. No. 4,687,667.

The currently available delayed release single-unit dosage forms containing enteric-coated peppermint oil have another limitation. They dump their primary active ingredient, L-menthol, when the enteric layer disintegrates. The terminal half-life of L-menthol is ~1.34 hours. Therefore, the systemic exposure of L-menthol is limited to approximately 4 hours, resulting in the need for frequent dosing (usually three times a day) to relieve the symptoms of IBS. The peppermint oil is usually dissolved in cooking oil to slow the release of L-menthol into the aqueous phase. However, cooking oil can aggravate the symptoms of IBS and the rate of release from the cooking oil is dependent on the diameter of the droplets of the oil. The diameter of the oil droplets is controlled by the presence of surfactants (bile acids etc.) and other oily substances in the stomach. With a multiparticulate delivery system, the individual particles pass through the pylorus over a longer period (approximately 90 minutes) and release their content steadily over this time period. The use of a single-unit non-disintegrating delayed release dosage form is undesirable because they release (dump) their active ingredient immediately after the single unit's enteric layer is dissolved.

In U.S. patent publication 2012/0207842, we described enteric coated multiparticulate L-menthol compositions adapted to overcome the drawbacks associated single-unit dosage forms. In order to prevent the L-menthol from sublimating as the cores were being processed, we resorted to low temperature processing techniques. The L-menthol multiparticulate compositions described in that application provided the release profile that we desired and worked well for some applications, but were not optimized for all applications.

We have identified a need for a multiparticulate L-menthol-containing formulation that avoids the drawbacks associated with single-unit enteric coated capsules and can be made using conventional room temperature processing techniques

SUMMARY

An aspect of the invention is to provide an L-menthol multiparticulate formulation with an enteric coating, using high-purity L-menthol. Such a formulation comprises a plurality of individual enteric coated cores containing L-menthol from an at least 80% pure L-menthol source, the enteric coated cores being effective to release at least about 35% of the L-menthol within about two hours, and at least about 80% of the L-menthol within about eight hours after being placed in an environment having a pH of between 5 to 8.

The enteric coated cores may further comprise a proton pump inhibitor, green tea extract, anti-inflammatory, and/or immune suppressor.

A continuous proteinaceous subcoating layer may cover the individual cores and separate the individual cores from their respective enteric coatings. A preferred proteinaceous subcoating comprises a gelatin film adhered to the core. The continuous proteinaceous subcoating may comprises a dried proteinaceous gel. The continuous proteinaceous subcoating is adapted to prevent the L-menthol from mixing with the enteric coating or forming L-menthol whiskers in the dosage form during storage.

The enteric coating may have a glass transition temperature higher than a standard boiling point of the peppermint oil.

The L-menthol may be dissolved in a solubilizing oil, which may contain one or more terpenes such as caraway oil and peppermint oil.

The enteric coated cores may further comprise an antioxidant effective for preventing L-menthol oxidation.

In a preferred embodiment, the enteric coated cores comprise about 10% w/w to about 70% w/w L-menthol.

The enteric coated cores may further comprise epigallocatechin gallate (EGCG) or a green tea extract with a high EGCG content.

In a preferred embodiment of the multiparticulate composition, the cores comprise about 10% w/w to about 35% w/w L-menthol, about 40% w/w to about 75% w/w microcrystalline cellulose, about 2% w/w to about 10% w/w methyl cellulose, and about 0.05% w/w to about 20% w/w of croscarmellose sodium; the subcoating comprises about 3.5% w/w to about 35% w/w of the uncoated cores; and the enteric coating comprises about 2% to about 35% w/w of the uncoated cores.

In a first method aspect of the invention, a method of making a multiparticulate formulation comprises blending L-menthol from an at least 80% pure L-menthol source, microcrystalline cellulose, a hydrophilic binder, and water to form a wet mass; extruding the wet mass to form an extrudate; dividing the extrudate into individual wet cores; drying the wet cores to form dried cores; and applying a subcoat followed by an enteric coating to the dried cores.

The hydrophilic binder may be selected from cellulose-based binder, starch based binder, povidone based binder, or a combination thereof.

A particularly preferred hydrophilic binder is methyl cellulose.

The method may further comprise coating the dried cores with a liquid proteinaceous material and drying the liquid proteinaceous material to form sub-coated cores prior to applying the enteric coating. The liquid proteinaceous material may comprises gelatin, such as a solution containing at least about 35% gelatin.

Coating the dried cores with a liquid proteinaceous material may comprise spraying the liquid proteinaceous material onto the dried cores.

The enteric coated cores are preferably spheroidal and not more than 3 mm in diameter.

The wet mass may further comprise caraway oil, peppermint oil, a PPI, an anti-inflammatory (such as the 5-ASA class), an immune suppressor (such as corticosteroids), or a green tea extract enriched in epigallocatechin gallate. In a second method aspect of the invention, a method of treating a gastrointestinal disorder in a subject comprises administering to the subject a multiparticulate formulation comprising a plurality of individual enteric coated cores containing L-menthol from an at least 80% pure L-menthol source, the enteric coated cores being effective to release at least about 35% of the L-menthol within about two hours, and at least about 80% of the L-menthol within about eight hours after being placed in an environment having a pH of 5 to 8.

Administering may be performed enterally.

The multiparticulate formulation may be blended with an acidic vehicle prior to being administered.

The L-menthol in the enteric coated cores may be dissolved in caraway oil, with or without a proton pump inhibitor, which is particularly useful to treat functional dyspepsia and/or gastroparesis.

The L-menthol in the enteric coated cores may be dissolved in peppermint oil, which is particularly useful to treat irritable bowel syndrome.

When the gastrointestinal disorder treated is inflammatory bowel disease, it may be beneficial if the enteric coated cores further contain one or more of epigallocatechin gallate (or green tea extract containing EGCG), an aminosalicylate, or a corticosteroid.

These and other objects, aspects, and advantages of the present invention will be better appreciated in view of the drawings and following description of certain embodiments.

DETAILED DESCRIPTION OF PREFERRED EMBODIMENTS

Figure 1:
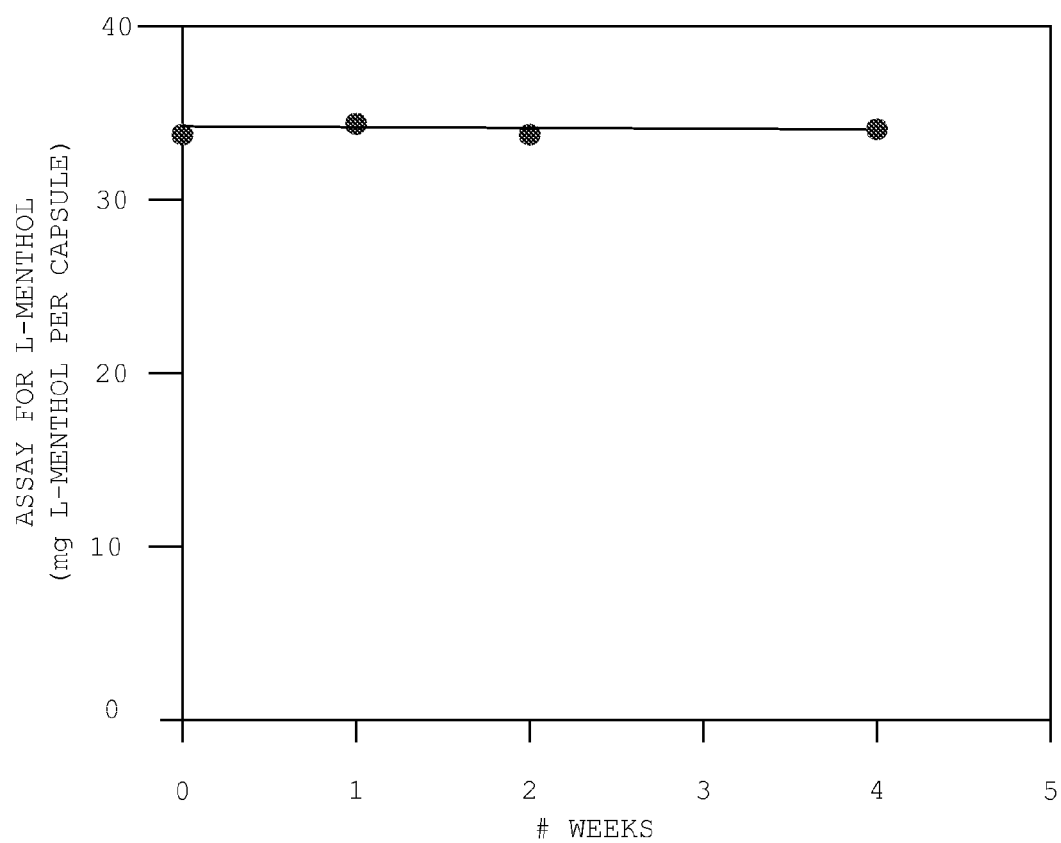
FIG. 1 is a graph showing the results of an accelerated stability assay for a multiparticulate formulation according to an embodiment of the invention stored at 40 degrees C. and 75% relative humidity for four weeks.

The Summary, Detailed Description of Preferred Embodiments, and the drawings refer to particular features (including method steps) of the invention. The disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein.

Because L-menthol is volatile, it is difficult to make L-menthol-containing dosage forms. Typical processing methods for making pharmaceutical dosage forms involve heating, which conventional wisdom suggests one should avoid when using volatile ingredients. We found that it is very difficult to make stable multiparticulate L-menthol containing compositions for this and other reasons. The volatile nature of L-menthol, along with its relatively unique property of forming whiskers on the surface of multiparticulates when the formulations are stored at above room temperature, poses a special challenge for enteric coated multiparticulates. The L-menthol whiskers that form on the surface of the enteric coated multiparticulate (within the capsule or sachet/stick type dosage forms) can result in appearance failures and dissolution failures under acid conditions.

As with peppermint oil, smooth muscle contractions in the gastrointestinal tract can be inhibited using L-menthol, the main bioactive component in peppermint oil. Peppermint oil derived from *Mentha piperita* only contains up to 50% menthol and *Mentha arvensis* contains only approximately 70-80% menthol. The other components of peppermint oil include menthone, pulegone, menthofuran, cineole, methyl acetate and limonene. There is significant variation in the relative composition of these other components based on the phenotype of the plant, geographic production area and harvest time. Also, some of these components may not be active thereby result in needing higher doses of peppermint oil versus doses of L-menthol, to get the same activity. In contrast to peppermint oil, which is primarily available as a liquid, L-menthol is available in liquid and crystalline powder forms. We have advantageously developed a unique combination of ingredients and processing methods for providing an enteric coated multiparticulate formulation comprising L-menthol from an at least 80% pure L-menthol source.

The multiparticulate formulation aspect of the invention is first described. The multiparticulate formulation is adapted to carry L-menthol to the intestines and includes a plurality of particulates that are preferably spheroidal in shape and are sized to fit through the pyloric sphincter when it is in a relaxed state. The diameter of each particulate is preferably in the range of about 0.1 mm to about 3 mm or, about 1 mm to about 2.5 mm, or less than about 1.4 mm. Particulates of this diameter are advantageous because they can fit through the pyloric sphincter and do not remain in the stomach as long as single-unit capsules, thereby providing a more reliable onset of action.

The multiparticulate composition includes a plurality of individual L-menthol containing cores that are each enteric coated. The enteric coating allows the individual cores to pass through the stomach without releasing a substantial amount of L-menthol. In the pH of the intestines, the enteric coating dissolves, exposing the cores and allowing oil-menthol to be released.

The core contains the primary active ingredient L-menthol, but may also contain other secondary active ingredients such as one or more other terpene-based substances such as terpenes, terpenoids, and/or essential oils. Terpene-based substances that may be used as secondary active ingredients include but are not limited to peppermint oil, caraway oil, orange oil, ginger oil, turmeric oil, curcumin oil, and fennel oil, among others. These terpenes are also solubilizing agents for L-menthol. The L-menthol solubilized in other terpenes reduces the tendency of L-menthol to form whiskers.

In the crystalline form, L-menthol is substantially free of impurities and has a consistent composition. Although it may not always be necessary, it is preferred that the starting material for L-menthol appear as visually perceptible L-menthol crystals. A preferred concentration of L-menthol in the core is between about 10% to about 70% w/w.

Alternatively, the secondary active ingredient may be a non-terpene-based substance that helps relieve gastrointestinal disorder symptoms from their various actions. Examples of non-terpene secondary active ingredients include, but are not limited to, polyphenols such as green tea extracts and aloe vera powder among others. The primary active ingredient in green tea extract is epigallocatechin gallate.

Because L-menthol is not very soluble in water, it may be advantageous to include a solubilizing agent. Preferred solubilizing agents include oils, such as essential oils. Essential oils are particularly advantageous for two main reasons. First, L-menthol readily dissolves in essential oils. Second, some essential oils are synergistically effective to treat symptoms of certain gastrointestinal disorders.

Essential oils such as peppermint oil, caraway oil, orange oil, fennel oil, etc. are liquid at room temperature. They are usually formulated as liquids in a capsule, with an enteric-coating over the capsule. We discovered that essential oils can be mixed with a cellulosic filler and a binder to make a dough or wet mass, but the dough formed by simply mixing these materials together does not produce a core with the desired strength for subcoating and further processing. By adding water to the wet mass, we produced cores containing an essential oil that were robust enough for subsequent processing.

The core may also contain one or more antioxidants that can maintain the purity of the L-menthol and other active ingredients if used. This is useful because L-menthol can oxidize to form undesirable derivatives. Examples of antioxidants that may be used include, but are not limited to tocopherol (vitamin E,) BHT (butylated hydroxy toluene), BHA (butylayted hydroxy anisole), and ascorbic acid.

Microcrystalline cellulose, or "MCC," is a pharmaceutical excipient that is widely used as a disintegrant in solid oral dosage forms. MCC promotes the breakup of tablets in aqueous environments to enhance drug release. It does this by wicking moisture through the pores of the tablet, weakening the tablet and causing it to disintegrate. Since MCC is used as a disintegrant, its causes the active ingredients in the solid oral dosage form to be released faster than they would otherwise be released.

We found that MCC also functions as a release-controlling polymer for L-menthol and essential oils. Accordingly, the core may include MCC. This is especially useful when L-menthol is blended with an oil such as an essential oil, including peppermint oil and/or caraway oil. The MCC is effective to gradually release the L-menthol into the intestines rather than quickly dumping the entire dose in a small region of the intestines. Accordingly, the MCC in our multiparticulate L-menthol compositions performs the opposite function of a disintegrant and overcomes the dose-dumping drawback held by the conventional single-unit enteric coated capsules. The blending of the L-menthol with caraway or peppermint oil also reduces the likelihood of forming L-menthol whiskers, which can lead to appearance and dissolution failures.

In such an embodiment, L-menthol is dissolved in the essential oil and is then combined with MCC and a hydrophilic binder such as a cellulose-based, starch-based, and/or povidone-based binder. It is to be understood that "cellulose-based," "starch-based" binders, and "povidone-based" binders includes cellulose, starch, and povidone derivatives. When mixed with water, the hydrophilic binder swells to form a hydrogel matrix. In contrast, MCC, L-menthol, and the oil are hydrophobic.

Examples of cellulose-based binders include methylcellulose based polymers, including, for example, methylcellulose and hydroxypropyl methylcellulose. Methylcellulose is particularly preferred for use in the composition.

When water is added to the core during processing, these materials separate into a hydrophobic phase and hydrophilic phase. The hydrophobic phase contains L-menthol and the oil dispersed in the microcrystalline cellulose based gel and the hydrophilic phase contains the hydrophilic binder. The L-menthol dissolved in the oil is dispersed throughout the hydrophobic phase.

One of the advantages of dispersing the solubilized L-menthol in MCC is that it allows excess water to be removed from the cores without also removing a substantial amount of the L-menthol. Conventional drying techniques would cause the L-menthol and oil in the core to evaporate with the water. Thus, by making the core to include a hydrophobic phase containing L-menthol dispersed in a microcrystalline cellulose-based gel and a hydrophilic phase containing a hydrophilic binder, the core can be processed without risking substantial loss of the L-menthol.

The core may also include pharmaceutically acceptable fillers, stabilizers, binders, surfactants, processing aids, and/or disintegrants. By way of example only, suitable materials for performing these functions are provided.

Preferred fillers include cellulosic filler materials such as microcrystalline cellulose, dibasic calcium phosphate, and/or another pharmaceutically acceptable filler.

Preferred binders include cellulosic water soluble polymers such as methylcellulose, starch, hydroxypropyl cellulose, gelatin, polyvinylpyrrolidone, polyethylene glycol, and/or another pharmaceutically acceptable binder.

Suitable processing aids include pharmaceutically acceptable processing aids for improving the flowability of the core materials during processing. Preferred processing aids include, but are not limited to, colloidal silicon dioxide, talc, magnesium stearate, stearin, and/or another pharmaceutically acceptable processing aid.

Preferred disintegrants include, but are not limited to, croscarmellose sodium, polyvinylpyrrolidone (crospovidone) sodium starch glycolate, and/or another pharmaceutically acceptable disintegrants.

We note, here, that using a disintegrant is particularly useful for the formulations in which L-menthol and the solubilizing oil are dispersed in the MCC-based gel. This is because the core may not release L-menthol fast enough for optimal treatment of some gastrointestinal disorders, such as FD (classified as a gastro-duodenal disorder) which require release in the duodenum, or Crohn's disease which requires release in the ileum or ulcerative colitis (classified as a colonic disorder) which require release in the colon. Adding a disintegrant speeds up the release of L-menthol from the core when the core reaches the desired area of the intestines.

The core may also include other active ingredients that behave synergistically with L-menthol to treat gastrointestinal disorders. These other active ingredients include drugs typically used to treat various gastrointestinal issues including proton pump inhibitors (for FD), anti-inflammatories (for IBD), and immune suppressors (IBD). Combining L-menthol with these other active ingredients improves their efficacy because of synergies in pharmacological activity and because L-menthol enhances their permeation into the intestinal walls.

Examples of PPIs include, but are not limited to omeprazole, lansoprazole, dexlansoprazole, esomeprazole, pantoprazole, rabeprazole, and ilaprazole. Including a PPI is preferred when the L-menthol in the core is dissolved in caraway oil.

Examples of anti-inflammatory drugs include aminosalicylates, including 5-aminosalicylate (5-ASA). Examples of 5-ASA are sulfasalazine, mesalamine, olsalazine and balsalazide. These work by decreasing the inflammation at the level of the lining of the gastrointestinal tract. However they do not address the pain and other symptoms associated with ulcerative colitis or Crohn's disease. The 5-ASAs are poorly absorbed. They are more effective when they are released and locally delivered to the ileum (for Crohn's disease) or colon (for ulcerative colitis). The L-menthol in combination with aminosalicylates (in the core) and with an enteric coat specific for delivery at the appropriate pH between pH 6.8 and 7.5 is useful for treating gastrointestinal disorders. We expect this combination to be synergistic in addressing the needs of the patients with the above disorders. Enteric coatings suited to these PPI-containing formulations include hypromellose acetate succinate coatings such as AQOAT AS-HF, AQOAT AS-HG, and poly(meth)acrylate-based coatings such as EUDRAGIT FS 30D or EUDRAGIT S-100).

Examples of immune suppressors include corticosteroids such as budesonide, prednisone, prednisolone and methylprednisolone. Corticosteroids non-specifically suppress the immune response. These drugs have significant short- and long-term side effects. They need to be delivered to the ileum (for Crohn's disease) or colon (for ulcerative colitis) for maximum efficacy. A combination of L-menthol with budesonide, prednisone, prednisolone or methylprednisolone, formulated in the core, with an enteric coat specific for delivery at the appropriate pH between pH 6.8 and 7.5 is useful for treating gastrointestinal disorders, such as ulcerative colitis or Crohn's disease. This synergistic activity may allow the patient to receive a lower dose of the corticosteroid in combination with L-menthol as compared to the corticosteroid by itself. The unique activities of L-menthol help relieve abdominal pain, cramps, and diarrhea. Enteric coatings suitable for these immune suppressor-containing formulations include AQOAT AS-HF, AQOAT AS-HG, EUDRAGIT FS 30D or EUDRAGIT S-100.

In a particular embodiment of the multiparticulate formulation, the enteric coated cores comprise about 10% w/w to about 35% w/w of L-menthol, about 40% w/w to about 75% w/w microcrystalline cellulose, and about 2% w/w to about 10% w/w methyl cellulose, and about 0.05% w/w to about 20% w/w of croscarmellose sodium; the subcoating comprises about 3.5% w/w to about 35% w/w of the uncoated cores; and the enteric coating comprises about 2% to about 35% w/w of the uncoated cores. Here, the % w/w/ refers to the % w/w/ of the uncoated cores.

Because it is often desirable to be able to ship products in non-refrigerated vehicles and store them for a long period of time, we preferred for our L-menthol-containing multiparticulate formulation to be stable when stored at 40 degrees C. and 75% relative humidity, from between 1 day to 30 days, and even longer. This would also be useful if the multiparticulate composition is distributed in hotter regions such as climate zone IV regions.

While developing multiparticulate compositions containing terpene-based active ingredients, we found that volatile ingredients sometimes penetrated the conventional subcoating materials we used to separate the cores form their enteric coatings. Because of this, the active ingredients would come in contact with the enteric coating if the temperature was elevated (25 degrees C.-50 degrees C.) or the composition was stored for a long period of time. This somewhat reduced the effectiveness of the enteric coating and amount of active ingredient in the core.

We solved this problem by developing a new subcoating material that may be applied to the finished core and prevents volatile active ingredients in the core from leaving the core and permeating the enteric coating at elevated temperatures. The subcoating includes a proteinaceous material that is applied along each core's exterior surface to form a substantially continuous thin film that forms a barrier between the core and the enteric coating that is applied after the subcoating.

Examples of proteinaceous materials that may be used in the subcoating include proteins such as, but not limited to casein, whey protein, soy protein, and various types of gelatin (Type A, Type B or derivatives of gelatin) or proteinaceous materials that have protein-like structures. A particularly preferred material used to form the subcoating is a solution containing at least about 50% of the proteinaceous material dispersed in a solvent. The solvent is preferably, but not necessarily water. A particularly preferred proteinaceous material is Type A gelatin.

The proteinaceous subcoating is preferably applied to the core in liquid form and subsequently dried on the core. When dry, the subcoating adheres to the core. Examples of the liquid form of the proteinaceous subcoating material include melts and gels. When dry, the subcoating forms a continuous film over the core and provides a barrier between the core and enteric coating.

Gelatin typically melts at about 35 degrees C., which is below the normal human body temperature of about 37 degrees C. Given this, one might expect that, if a multiparticulate composition, including a gelatin subcoating, is heated above 35 degrees C., the subcoating will melt and release the active ingredients from the core. We observed, however, that gelatin subcoated multiparticulate compositions did not release the terpene-based active ingredients from the core even when heated above 35 degrees C. This is a particularly unexpected result that provides numerous advantages.

Because the proteinaceous subcoating prevents volatile ingredients from being released from the core even when heating above the melting point of the proteinaceous material, by applying the proteinaceous subcoating, one does not have to avoid heating the subcoated cores during processing. One scenario in which this is advantageous is when the enteric coating is applied. Enteric coating polymers have a glass transition temperature ($T_g$) that is often above 35 degrees C. After being applied to a core, enteric coated particulates are preferably heated above $T_g$ so that the enteric coating polymer can cure, thereby achieving optimum enteric protection of the core. Thus, using the proteinaceous subcoating between the core and enteric coating allows one to achieve optimum enteric protection without releasing the L-menthol from the core.

The subcoating may be applied to the core as a gelatin-containing subcoating solution. The solvent may be any solvent in which gelatin is soluble, such as water. In a preferred embodiment, the subcoating solution comprises about 5% to about 30% w/w gelatin and about 70% to about 95% solvent. When the subcoating solution is allowed to dry around the core, the solvent evaporates, leaving a thin gelatin film that adheres to the core and forms a barrier between the core and enteric coating. The gelatin film subcoating is preferably about 3.5% w/w to about 35% w/w of the enteric coated particulates. Surprisingly, in our experiments, drying cores containing peppermint oil and water, at about 15 degrees C. to about 25 degrees C. did not result in significant loss of the L-menthol as the water was being removed by fluid bed drying.

The enteric coating is applied over each core, or, if a subcoating is used, over the subcoating. In a preferred embodiment, the enteric coating is about 2% w/w to about 35% w/w of the enteric coated particulate. A preferred enteric coating material is a methacrylic acid based material such as a methacrylic acid based co-polymer. These materials may be combined with other materials such as plasticizers for forming an enteric coating solution. In a typical embodiment, the enteric coating solution comprises about 5% w/w to about 35% w/w water, and the enteric-coated dried multiparticulates contain 0.5% w/w to about 5% w/w plasticizer, about 0.05% w/w to about 5% w/w anti-adherent, and about 2% w/w to about 35% w/w methacrylic acid copolymer. By way of example only, a suitable plasticizer is triethyl citrate and a suitable anti-adherent is PLASACRYL T20 (Emerson Resources, Inc., Norristown, Pa.). PLASACRYL T20 is an emulsion of anti-tacking agent and plasticizer and contains water, glyceryl monostearate, triethyl citrate and polysorbate 80. The enteric coating is preferably about 3.5% w/w to about 35% w/w of the enteric coated particulates.

The enteric coating material is selected to allow the L-menthol to be released in a preferred section of the intestines. By way of example, for the L-menthol to release in the colon, a sodium aliginate/ethyl cellulose enteric coating may be used or an alternative enteric coating material that dissolves at close to pH 7.0.

If the proteinaceous subcoating is not used, it is preferred that the enteric coating material be applied to the core without heating the core above about 30 degrees C. so that the L-menthol does not degrade or volatalize. This can be particularly difficult considering that enteric coatings are typically applied in a fluidized bed coater at sufficient air inlet temperature to result in a product temperature of about 38-42 degrees C. Unfortunately, at such a high temperature, L-menthol tends to degrade and volatilize. This made it very difficult to produce a high purity, solid L-menthol formulation that met or approximated the desired USP 711 enteric specifications. We found that both EUDRAGIT L30D-55 and KOLLICOAT MAE 30 DP were suitable because they could be reliably applied to the cores at lower temperatures with good coalescence between the enteric coating and the underlying material. KOLLICOAT MAE 30 DP is a methacrylic acid-ethyl acrylate co-polymer. Without intending to be bound by theory, this may be because the glass transition temperature $T_g$ of these methacrylic acid based copolymers is roughly about 26° C. and depends on the plasticizer used. These methacrylic acid copolymer based enteric coating materials do not require pH sensitive pore formers to dissolve at or near neutral pH.

The enteric-coated particulates may be coated with a finish coat. The finish coat is used, for example, to overcome the mucoadhesive properties of some enteric coating materials, which make the multiparticulates stick together during processing, storage, or dispensing through a tube for enteral feeding. The finish coat is preferably a cellulosic derivative such as HPMC (hydroxylpropyl methylcellulose), HPC (hydroxyl propyl cellulose), CMC (carboxy methylcellulose), or another pharmaceutically acceptable finish coating material. When used, the finish coat is preferably about 1% to 10% w/w of the finished multiparticulate.

A particularly preferred finish coat material is HPMC because is not mucoadhesive. As such, it prevents the multiparticulates from sticking to the stomach wall as well as food in the stomach. This allows the multiparticulates to reach the intestines quickly, making the onset of action more reliable than the single-unit capsules.

The release profile of L-menthol in the body can be varied to treat different disorders. L-menthol can be used to treat a plethora of gastrointestinal disorders such as irritable bowel syndrome, inflammatory bowel disease (ulcerative colitis and Crohn's disease), gastroparesis, and functional dyspepsia, but it is best to release the active ingredients at a certain point in the gastrointestinal tract to optimally treat each disorder.

To treat gastrointestinal disorders associated with irritable bowel syndrome, the multiparticulate composition is formulated to minimize the amount of L-menthol released into the stomach and colon, so that most of it is released in the small intestine. Preferably, 20% or less of the L-menthol is released into the stomach and 20% or less of the L-menthol is released into the colon. Also, in many instances such as IBS, the L-menthol is preferably gradually released from the cores over about 4 to about 6 hours after the cores pass the pyloric sphincter into the small intestine in order to deliver the active ingredients locally in the small intestine. This release profile treats gastrointestinal disorders by stabilizing the digestive system and alleviating the symptoms associated with disorders such as irritable bowel syndrome.

To treat a gastrointestinal disorder such as functional dyspepsia (classified as a gastro-duodenal disorder), the multiparticulate composition is formulated so that the L-menthol or peppermint oil, dissolved in caraway oil, is rapidly released after the multiparticulates pass through the stomach and the pylorus, over the course of about 0 to about 2 hours in order to deliver L-menthol or peppermint oil plus caraway oil locally to the duodenum section of the small intestine to help stabilize the digestive system and/or alleviate the symptoms associated with functional dyspepsia.

Functional dyspepsia is recognized as a gastro-duodenal disorder (category B) according to the Rome III classification system. Preferably, 20% or less of the L-menthol or peppermint oil plus caraway oil is released in the stomach and 20% or less of the peppermint oil is released in the jejunum and ileum sections of the small intestine (which follow the duodenum) and the colon.

To treat a gastrointestinal disorder such as inflammatory bowel disease (including ulcerative colitis or Crohn's disease), the multiparticulate composition is formulated so that the L-menthol is rapidly released after the multiparticulates pass through the stomach and the first 2 sections of the small intestine (i.e. duodenum and jejunum, over the course of about 4 to about 6 hours, in order to deliver the L-menthol locally to the ileum or colon to attenuate the inflammatory response and/or alleviate the symptoms associated with inflammatory bowel disease. Preferably, 30% or less of the oil-menthol is released in the stomach and the first 2 sections of the small intestine and greater than 70% of the peppermint oil is released in the first 2 hours after the multiparticulates reach the pH of the ileum or colon.

In a particularly preferred embodiment, the enteric coated cores of the multiparticulate composition release at least about 35% of the L-menthol within about two hours, and at least about 80% of the L-menthol within about eight hours after being placed in an environment having a pH of 5 to 8.

It should be understood that where this disclosure makes reference to treating a gastrointestinal disorder, that the terms "treat," "treating, or any other variation of the word "treat," includes prevention or management of the gastrointestinal disorder. When MCC is used as a release-controlling polymer, the core formulation allows one to achieve a suitable release profile. One skilled in the art will recognize that that the release rate of L-menthol from the core can be adjusted by including a disintegrant, that actually functions as a disintegrant, or another conventional release controlling polymer.

A daily dose of a multiparticulate composition containing L-menthol is about 20 mg to about 1200 mgs of L-menthol, split into two or three doses per day. Each dosage form may contain between 10 mgs and 140 mgs of L-menthol, more preferably, about 90-110 mg of L-menthol.

Doses of the multiparticulate composition may be administered sporadically when needed for treating acute disruptions of the gastrointestinal tract or may be administered as part of a long term regimen for treating GI disorders such as irritable bowel syndrome, functional dyspepsia, gastroparesis, or inflammatory bowel disease. A treatment subject may be a human or animal.

The enteric coated multiparticulates may be prepared into a suitable pharmaceutical or medical food dosage form such as a capsule, tablet or sachet, or are mixed with an acidic food vehicle and directly fed through a feeding tube. A typical dosage form contains about 400 mg of the particulates, but, depending on the desired dosage, this amount may be adjusted. Acidic food vehicles include juices and foods such as, for example, apple sauce and apple juice.

The multiparticulate formulation is preferably formulated to be administered enterally, such as orally or through a feeding tube, to a human or animal subject to ensure that the subject receives an effective amount of L-menthol or peppermint oil over the course of several hours after ingestion. The feeding tube may help with subjects that have achalasia, dysphagia, or another disorder that does not allow them to administer a capsule orally with water. Alternatively the multiparticulates can be sprinkled onto apple sauce for patients that cannot swallow larger sized capsules.

A preferred method of making the multiparticulate formulation is now described. The core is typically prepared by wet granulating the core materials into a wet mass, extruding the wet mass to form an extrudate, breaking the extrudate into a plurality of core pieces, and spheronizing the core pieces. The spheronized core pieces are then dried in a dryer such as a fluid bed dryer to remove the water. If desired the dried spheronized cores are then sieved to separate cores of different sizes.

The dried spheronized cores are then coated with the proteinaceous subcoating material if desired. One way to apply the subcoating material to the cores is to prepare a subcoating solution and spray the subcoating solution onto the cores. There are various conventional methods for doing this, but the preferred method is Wurster coating or fluid bed coating (top spray or bottom spray). The subcoating solution is subsequently allowed to dry over the cores, leaving each core coated with a thin, continuous proteinaceous film. If desired, the subcoated cores are sieved to separate them into different sizes.

The enteric coating is then applied to the subcoated cores or directly to the cores if no subcoating is used. One means of applying the enteric coating is to spray it onto the subcoated cores. There are various conventional methods for doing this, but the preferred method is Wurster coating or fluid bed coating. The enteric coated particulates are subsequently dried. During the enteric coating process, the cores are preferably heated in an environment that is about 20 degrees C. to about 50 degrees C. to cure the enteric coating materials above their $T_g$.

A finish coating may be applied over the enteric coated particulates if desired. One way to apply the finish coating is to spray it onto the enteric coated cores. There are various conventional methods for doing this, but the preferred method is Wurster coating or fluid bed coating.

A more particular method of making the multiparticulate formulation involves blending L-menthol from an at least 80% pure L-menthol source dissolved in an oil, microcrystalline cellulose, cellulose hydrophilic binder, croscarmellose sodium and water to form a wet mass; extruding the wet mass to form an extrudate; dividing the extrudate into individual wet cores; drying the wet cores to form dried cores; and applying an enteric coating to the dried cores.

Another method aspect of the invention is a method of treating a gastrointestinal disorder in a subject. The method involves administering to the subject, a multiparticulate formulation comprising a plurality of individual enteric coated containing L-menthol from an at least 80% pure L-menthol source, the enteric coated cores being effective to release at least about 35% of the L-menthol within about two hours, and at least about 80% of the L-menthol within about eight hours after being placed in an environment having a pH of 5 to 8. The multiparticulate composition can be enterally administered through use of a conventional oral dosage form such as a tablet, caplet, capsule, sachet, or multiparticulate administered through a feeding tube, among others. The term "subject" includes human and animal subjects.

Another enteral means for administering the multiparticulate composition orally is by adding it to food. In this instance, the multiparticulate composition is blended with an acidic food vehicle such as apple sauce or apple juice or another acidic vehicle that prevents premature release of the active ingredients and is then ingested by the subject.

The L-menthol-containing multiparticulate formulations may be used as medical foods for the dietary management of various gastrointestinal disorders or as medicaments.

Some of the multiparticulate formulations are geared to treat certain gastrointestinal disorders. When the enteric coated cores include L-menthol dissolved in caraway oil (with or without a PPI), the formulation is suited to treat functional dyspepsia. When the enteric coated cores include L-menthol dissolved in peppermint oil, the formulation is suited to treat irritable bowel syndrome. When the enteric coated cores include L-menthol and one or more of green tea extract enriched with epigallocatechin gallate, aminosalicylate, or corticosteroid, the formulation is suited to treat inflammatory bowel disease, including ulcerative colitis and Crohn's disease.

Examples

This section provides specific examples of the multiparticulate composition and method aspects of the invention. These examples are provided to illuminate certain preferred aspects and embodiments of the invention, but the scope of the invention is not limited to what these examples teach.

Example 1

Preparation of a Multiparticulate Formulation

The core was prepared using microcrystalline cellulose (MCC) commercially available under the name AVICEL® PH 102 (FMC Corp., Philadelphia, Pa.), methylcellulose commercially available under the name METHOCEL® A15LV (Dow Chemical Co., Midland, Mich.), L-menthol, and USP purified water.

33.25 kg MCC, 1.75 kg methylcellulose, and 15 kg L-menthol were blended with water to form a wet mass. The wet mass was granulated in a high shear granulator. The granulated wet mass was then extruded and spheronized. The spheronized particles were subsequently dried in a fluid bed dryer to form uncoated cores. The drying temperature was about 16 degrees C. to 20 degrees C.

The uncoated cores were Wurster coated with 37 kg of a subcoating composition containing about 15% acid bone gelatin and 85% USP water and dried.

The subcoated cores were Wurster coated with 31 kg of a 20% w/w enteric coating suspension containing KOLLICOAT® MAE 30 DP, PLASACRYL T20, triethyl citrate USP, and purified water USP. The dry solids weight of amount KOLLICOAT® MAE 30 DP was approximately 5.4 kg. The dry solids weight of triethyl citrate was approximately 0.28 kg. The dry solids weight of PLASACRYL T20 was approximately 0.5 kg. The enteric coated cores were then dried at about 40 degrees C.

The enteric coated cores were Wurster coated with 26 kg of a finish coat solution containing about 10% w/w hydroxyl propyl methyl cellulose and 90% water USP and dried at about 40 degrees C.

Example 2

Stability Testing of the Multiparticulate Formulation of Example 1

The multiparticulate composition described in Example 1 was subsequently tested to ensure that the gelatin subcoating prevented the L-menthol from evaporating and leaving the core when stored at elevated temperatures over a long period of time.

In the first set of experiments, we prepared capsules containing the multiparticulate composition and stored them at 40 degrees C. and 75% relative humidity for four weeks. Each week, we measured the amount of L-menthol in a selection of the capsules. FIG. 1 shows the results of this study as a graph of the number of milligrams of L-menthol per capsule as a function of time. The results show that the amount of L-menthol in the capsules remained more or less constant at about 34 mg during the four week period. This proves that the gelatin subcoating maintains the integrity of the core.

In the second set of experiments, we simulated the gastrointestinal environment and measured the dissolution profile of the multiparticulate composition to ensure that the enteric coating worked and that almost all of the L-menthol would be released from the core within about 8.5 hours. This was a conventional two stage dissolution study in which the sample was placed in an acidic medium (0.1 N HCl) for about two hours and subsequently placed in a neutral medium (pH=6.8) for the remainder of the time.

Figure 2:
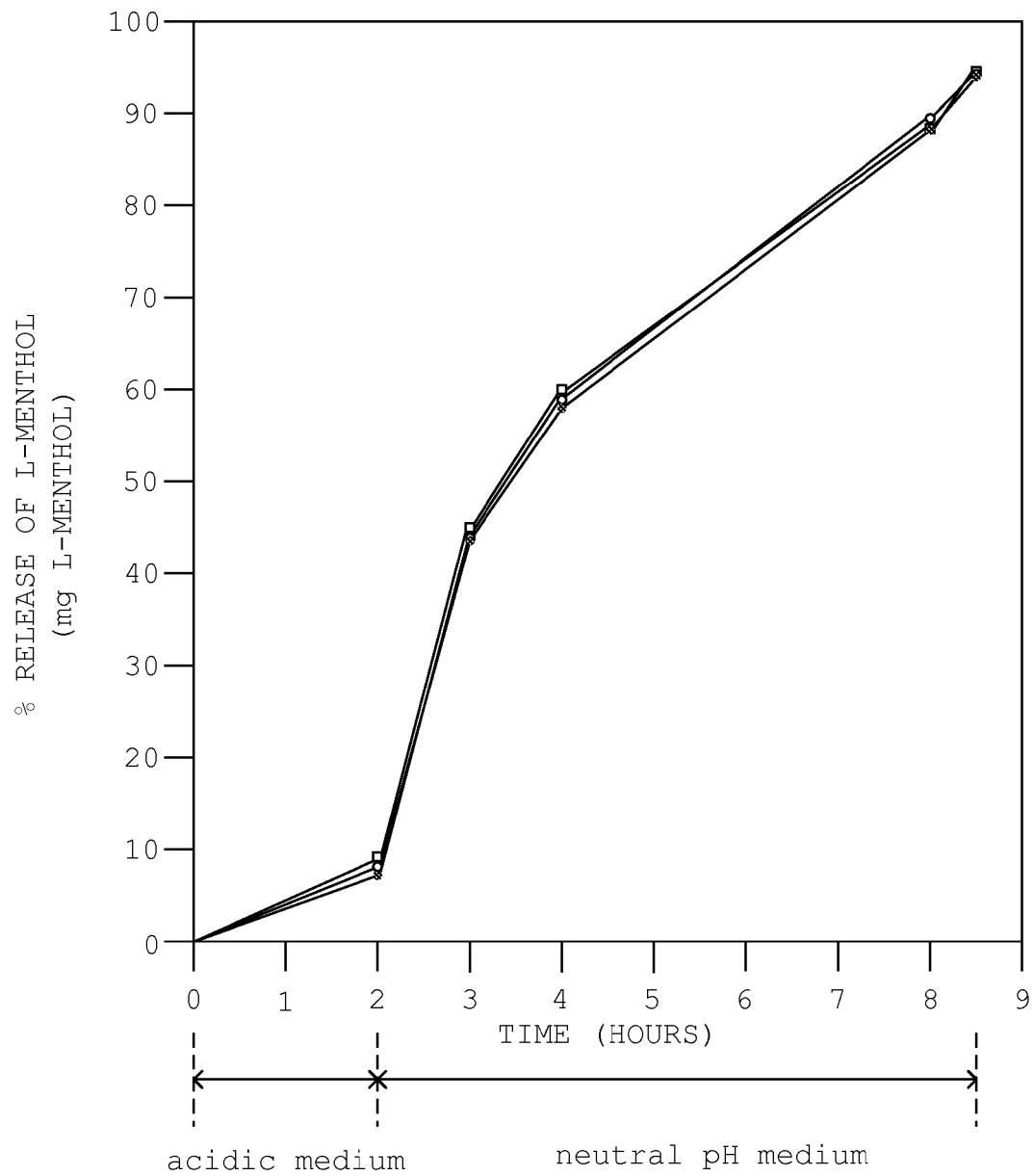
FIG. 2 is a graph showing the results of a two-stage dissolution test for a multiparticulate formulation according to an embodiment of the invention after the composition was stored at 40 degrees C. and 75% relative humidity.

The results of this experiment are shown in FIG. 2 as the % release of mgs of L-menthol over time. After two hours in the acidic medium, each of the samples tested had only released about 10% or less of the L-menthol, indicating that the enteric coating was intact and worked normally. Over the following 6.5 hours in the neutral medium, the L-menthol was gradually released from the core.

Example 3

Preparation of a Multiparticulate Formulation

This prospective example illustrates a method for making an L-menthol multiparticulate formulation, including a proteinaceous subcoating.

The core is made by blending 13 kg of solid L-menthol with 10 kg of caraway oil until the L-menthol dissolves. The L-menthol/caraway oil blend is mixed with 50 kg MCC, 2.7 kg methyl cellulose, and 7.5 kg croscarmellose sodium. 38.8 kg of water is added to the mixture to form the wet mass.

The wet mass is granulated in a high shear granulator. The granulated wet mass was then extruded and spheronized. The spheronized particles are subsequently dried in a fluid bed dryer to form uncoated cores. The drying temperature is about 16 degrees C.

The uncoated cores are Wurster coated with 203 kg of a subcoating composition containing about 15% acid bone gelatin and 85% USP water and dried.

The subcoated cores are Wurster coated with 56 kg of a 20% w/w enteric coating suspension containing KOLLICOAT® MAE 30 DP, PLASACRYL T20, triethyl citrate USP, and purified water USP. The dry solids weight of amount KOLLICOAT® MAE 30 DP is approximately 8.24 kg. The dry solids weight of triethyl citrate is approximately 2.13 kg. The dry solids weight of PLASACRYL T20 is approximately 0.82 kg. The enteric coated cores are then dried at about 40 degrees C.

The enteric coated cores are Wurster coated with 36.9 kg of a finish coat solution containing about 10% w/w hydroxylpropyl methyl cellulose and 90% water USP and dried at about 40 degrees C.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

The specification discloses typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and in the claims.

That which is claimed is:

1. A multiparticulate dosage form comprising a plurality of individual spheroidal enteric coated particulates having (a) a diameter of 0.1 to 2.5 mm; (b) a solid core containing an effective amount of a combination of an L-menthol source and a terpene-based essential oil; (c) a continuous proteinaceous subcoating over the core; and (d) an enteric coating over the subcoating.

2. The multiparticulate dosage form of claim 1, wherein the effective amount is an amount effective for treating a gastrointestinal disorder.

3. The multiparticulate dosage form of claim 1, wherein the L-menthol source is at least 80% pure L-menthol.

4. The multiparticulate dosage form of claim 3, wherein the L-menthol source is crystalline L-menthol.

5. The multiparticulate dosage form of claim 4, wherein the crystalline L-menthol is dissolved in the terpene-based essential oil.

6. The multiparticulate dosage form of claim 5, wherein the terpene-based essential oil is peppermint oil.

7. The multiparticulate dosage form of claim 5, wherein the terpene-based essential oil is caraway oil.

8. The multiparticulate dosage form of claim 3, wherein the terpene-based essential oil is peppermint oil.

9. The multiparticulate dosage form of claim 3, wherein the terpene-based essential oil is caraway oil.

10. The multiparticulate dosage form of claim 1, wherein the proteinaceous subcoating is a dried proteinaceous gel.

11. The multiparticulate dosage form of claim 1, wherein the proteinaceous subcoating is a gelatin film.

12. The multiparticulate dosage form of claim 1, wherein the proteinaceous subcoating is a continuous coating of gelatin substantially surrounding the core.

13. The multiparticulate dosage form of claim 1, wherein:
the L-menthol source is crystalline L-menthol, the terpene-based essential oil is peppermint oil, and the L-menthol is dissolved in the peppermint oil;
the proteinaceous subcoating is a continuous coating of gelatin substantially surrounding the core; and
the enteric coating is a methacrylic acid based polymer material.

14. The multiparticulate dosage form of claim 1, wherein:
the L-menthol source is crystalline L-menthol, the terpene-based essential oil is caraway oil, and the crystalline L-menthol is dissolved in the caraway oil;
the proteinaceous subcoating is a continuous coating of gelatin substantially surrounding the core; and
the enteric coating is a methacrylic acid based polymer material.

15. A multiparticulate dosage form comprising a plurality of individual spheroidal enteric coated particulates having (a) a diameter of 0.1 to 2.5 mm; (b) a solid core containing an effective amount of a combination of an L-menthol source and EGCG; (c) a continuous proteinaceous subcoating over the core, and (d) an enteric coating over the subcoating.

16. The multiparticulate dosage form of claim 15, wherein the proteinaceous subcoating is a dried proteinaceous gel.

17. The multiparticulate dosage form of claim 15, wherein the proteinaceous subcoating is a gelatin film.

18. The multiparticulate dosage form of claim 15, wherein the proteinaceous subcoating is a continuous coating of gelatin substantially surrounding the core.

19. The multiparticulate dosage form of claim 15, wherein the L-menthol source is crystalline L-menthol.

20. The multiparticulate dosage form of claim 15, wherein the L-menthol source is at least 80% pure L-menthol.

21. The multiparticulate dosage form of claim 15, wherein:
   the L-menthol source is crystalline L-menthol;
   the proteinaceous subcoating is a continuous coating of gelatin substantially surrounding the core; and
   the enteric coating is a methacrylic acid based polymer material.

\* \* \* \* \*